United States Patent [19]
Cullinan et al.

[11] Patent Number: 5,599,822
[45] Date of Patent: Feb. 4, 1997

[54] METHODS FOR MINIMIZING BONE LOSS

[75] Inventors: George J. Cullinan, Trafalgar; Steven A. Fontana, Martinsville, both of Ind.

[73] Assignee: Eli Lilly and Company, Indianapolis, Ind.

[21] Appl. No.: 467,475

[22] Filed: Jun. 6, 1995

[51] Int. Cl.⁶ ............................ A61K 31/41; A61K 31/44; A61K 31/445
[52] U.S. Cl. ................ 514/324; 514/379; 514/422; 514/443; 514/579
[58] Field of Search ................... 514/379, 233.5, 514/324, 422, 443, 579

[56] References Cited

U.S. PATENT DOCUMENTS

| | | | |
|---|---|---|---|
| 3,135,743 | 6/1964 | Clinton et al. | 260/239.5 |
| 4,133,814 | 1/1979 | Jones et al. | 260/326.5 |
| 4,380,635 | 4/1983 | Peters | 546/202 |
| 4,418,068 | 11/1983 | Jones | 424/267 |
| 5,393,763 | 2/1995 | Black et al. | 514/333 |

OTHER PUBLICATIONS

Howel, A., et al., *The Lancet*, 345:29–30 (1995).

Primary Examiner—Joseph K. McKane
Attorney, Agent, or Firm—James J. Sales; David E. Boone

[57] ABSTRACT

The present invention provides a method for minimizing the bone loss effect of a compound of formula II

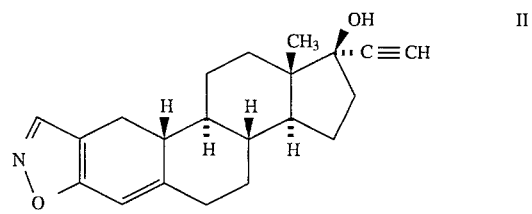

or a pharmaceutically acceptable salt thereof, wherein said formula II compound is administered to a mammal in need of treatment, comprising concurrently or sequentially administering to said mammal an effective amount of a compound of formula I

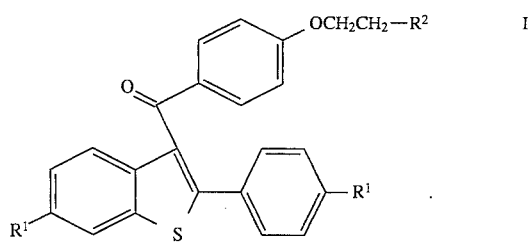

12 Claims, No Drawings

METHODS FOR MINIMIZING BONE LOSS

The present invention relates to the fields of pharmacology and pharmaceutical chemistry, and provides methods for minimizing the bone loss effect induced by the administration of certain pharmaceutical agents, and pharmaceutical compositions therefor.

Danazol (Danocrine®, Sterling), pregna-2,4-dien-20-ynol[2,3-d]isoxazol-17-ol, is an anabolic steroid derivative of ethisterone which is classified as an anterior pituitary suppressant having mild androgenic side effects. As such, danazol can cause masculization, while acting as an excellent inhibitor of estrogen production. When used for the treatment of endometriosis and other endocrine disorders [see, e.g., *Drugs*, 19:321–372 (1980)], the administration of danazol induces, particularly in cycling women, a postmenopausal state and its accompanying pathologies, particularly bone loss.

Traditionally, estrogen administration has been used to treat individuals suffering from naturally-occurring or induced bone loss. However, the administration of estrogen to an individual being treating with danazol for endometriosis or a related endocrine disorder would be contra-indicated. It, therefore, would be of great value to be able to take advantage of the distinct activity of danazol while minimizing the negative side effects associated with the use of danazol via the sequential or concurrent administration of another pharmaceutical agent.

The present invention, therefore, provides a method of minimizing the bone loss effect of danazol, wherein danazol is administered to a mammal in need of treatment, comprising concurrently or sequentially administering to said mammal an effective amount of a compound of formula I

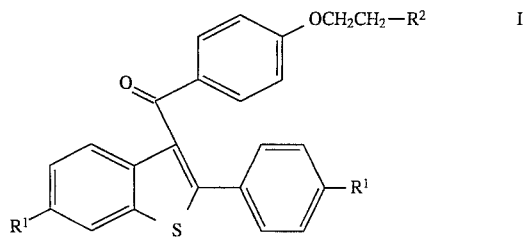

wherein
each $R^1$ is independently —H, —OH, —O($C_1$–$C_4$ alkyl), —OCOC$_6$H$_5$, —OCO($C_1$–$C_6$ alkyl), or —OSO$_2$($C_4$–$C_6$ alkyl); and
$R^2$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

Also provided by the present invention are methods for minimizing the bone loss effect of danazol via the coadministation (sequential or concurrent) of a bone anabolic agent, particularly parathyroid hormone (PTH) (1–84) or (1–34), with or without the coadministration of a formula I compound.

The present invention further provides pharmaceutical formulations comprising danazol and a formula I compound, with or without a bone anabolic agent, and danazol plus a bone anabolic agent, in combination with a pharmaceutically acceptable carrier, diluent, or excipient.

Danazol, a compound of formula II

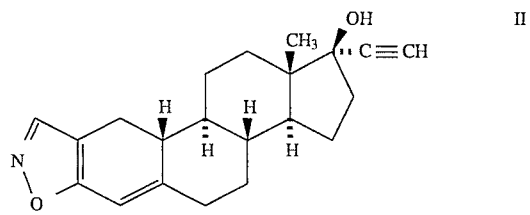

or a pharmaceutically acceptable salt thereof, is well known in the art and is prepared as taught, for example, in U.S. Pat. No. 3,135,743; and Manson, et al., *J. Med. Chem.,* 6:1 (1963).

Similarly, compounds of formula I

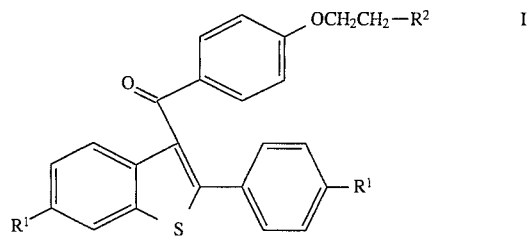

wherein
each $R^1$ is independently —H, —OH, —O($C_1$–$C_4$ alkyl), —OCOC$_6$H$_5$, —OCO($C_1$–$C_6$ alkyl), or —OSO$_2$($C_4$–$C_6$ alkyl); and $R^2$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof, are well known in the art and can be prepared according to established procedures, such as those detailed in U.S. Pat. Nos. 4,133,814; 4,418,068; and 4,380,635.

Compounds of formula I, particularly raloxifene, in which each $R^1$ is —OH and $R^2$ is 1-piperidinyl are classified as nuclear regulatory molecules. More particularly, raloxifene has been shown to bind to estrogen receptors and originally was demonstrated to have antiestrogenic activity because it blocked the ability of estrogen to activate uterine tissue and estrogen-dependent cancers. Indeed, raloxifene does block the action of estrogen in some cells but, in other cell types, it activates the same genes as estrogen activates and displays the same pharmacology. As a type II antiestrogen, raloxifene, and its analogs defined above as compounds of formula I, are tissue selective antiestrogens with mixed agonist-antagonist properties.

Bone anabolic agents are those agents which are known in the art to build bone by increasing the production of bone matrix protein. Such anabolic agents include, for example, the various forms of parathyroid hormone (PTH) such as naturally occurring PTH (1–84), PTH (1–34), analogs thereof, and the like, which are prepared via well known procedures.

As used herein, "bone loss" means a reduction of bone mineral density of cancellous bone, which frequently is a side-effect of danazol administration to mammals, and the term "minimize", or a derivative thereof, contemplates partial or complete inhibition and/or repair of danazol-induced bone loss.

The methods of the present invention can be tailored to counter the bone loss effect induced by the administration of danazol. For example, when administration of danazol is first initiated, particularly as an acute treatment, it is preferred to coadminister a compound of formula I, especially the hydrochloride salt of raloxifene, to counteract the potential bone loss. When administration of danazol will be for the treatment of a chronic malady (e.g., endometriosis), a formula I compound, preferably raloxifene hydrochloride, and an anabolic bone agent, particularly PTH (1–84) or PTH (1–34), may be coadministered at the time treatment with danazol is initiated, and throughout the course of therapy. However, if danazol is administered for a chronic malady without the coadministration a formula I compound, a bone anabolic agent may be coadministered with, or following, multiple courses of therapy with danazol. The particular method of the present invention which would optimize the minimization of bone loss induced by the administration of danazol is, therefore, dictated by the duration of danazol's course of therapy, and when administration of a compound of formula I, and/or a bone anabolic agent, is initiated relative to the commencement of therapy with danazol. In essence, the attending physician is best suited to determine whether a formula I compound and/or a bone anabolic agent should be administered, and whether the administration of such agents should be concurrent or sequential to the administration of danazol.

When administered sequentially, pharmaceutical formulations of danazol, compounds of formula I, and bone anabolic agents are prepared by methods known by one of ordinary skill in the art.

When administered concurrently, danazol, compounds of formula I and bone anabolic agents may be prepared into pharmaceutical formulations via the above-mentioned known methods, and administered as separate entities. Alternatively, they may be combined to form a pharmaceutical composition of the present invention which comprises danazol, or a pharmaceutically acceptable salt thereof, a compound of formula I, or a pharmaceutically acceptable salt thereof, and, optionally, a bone anabolic agent, in combination with a pharmaceutically acceptable carrier, diluent, or excipient.

The present invention also provides pharmaceutical compositions comprising danazol, or a pharmaceutically acceptable salt thereof, and a bone anabolic agent, in combination with a pharmaceutically acceptable carrier diluent, or excipient.

Preferred compounds of formula I and bone anabolic agents for pharmaceutical compositions of the present invention are the same as those preferred for the methods of the present invention.

Pharmaceutical compositions of the present invention can be prepared in unit dosage form for parenteral, transdermal, rectal, nasal, intravenous, or oral administration via conventional and well known techniques. Such compositions active ingredient of each desired combinant will be mixed with a carrier, diluted by a carrier, or enclosed within a carrier which may be in the form of a capsule, sachet, paper, or other container. When the carrier serves as a diluent, it may be a solid, semisolid, or liquid material which acts as a vehicle, excipient, or medium for the active ingredient. Thus, the compositions of the present invention can be in the form of tablets, pills, powders, lozenges, sachets, soft and hard gelatin capsules, sterile injectable solutions, and sterile packaged powders. As used herein, the term "active ingredient" refers to danazol, or a pharmaceutically acceptable salt thereof, a formula I compound, or a pharmaceutically acceptable salt thereof, and a bone anabolic agent, used in a pharmaceutical composition of the present invention.

Additionally, pharmaceutical agents of the present compositions are well suited for formulation as sustained release dosage forms and the like. The compositions can be so constructed that they release active ingredient only or preferably in a particular physiological location, preferably over a long period of time. The coatings envelop and protective matrices may be made, for example from polymeric substances or waxes.

More particularly, pharmaceutical compositions of the present invention which sequentially release, for example, an effective amount of danazol, followed by the release of an effective amount of a compound of formula I, and/or a bone anabolic agent, may be constructed as an implant device. Such an implant device would consist of an outer, rapidly degradable polymer, such as a low molecular weight wax, impregnated with danazot. The inner cone of the implant would be made of a slowly degradable polymer, such as a high molecular weight wax, impregnated with a compound of formula I and/or a bone anabolic agent.

Also included within the scope of the present invention are pharmaceutical compositions for transdermal delivery of the pharmaceutical agents used in the methods herein described. The preparation of such compositions are well known to one of ordinary skill in the art.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The compositions can additionally include lubricating agents, wetting agents, emulsifying and suspending agents, preserving agents, sweetening agents or flavoring agents. The compositions may be formulated so as to provide quick, sustained, or delayed release of the active ingredient(s) after administration to the patient by employing procedures well known in the art. For oral administration, a compound optionally including a second component compound, can be admixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects, each unit containing a predetermined quantity of active ingredients calculated to produce the desired therapeutic effect, in association with the required pharmaceutically acceptable carrier. By "pharmaceutically acceptable", it is meant the carrier, diluent, or excipient must be acceptable with the other ingredients of the formulation and not deleterious to the recipient thereof.

The following formulation and composition examples are only illustrative and are not intended to limit the scope of the present invention.

FORMULATIONS/COMPOSITIONS

Formulation 1: Gelatin capsules
Hard gelatin capsules are prepared using the following:

| Ingredient | Quantity (mg/capsule) |
| --- | --- |
| Danazol | 100–400 |
| Starch, NF | 0–650 |
| Starch flowable powder | 0–650 |
| Silicone fluid 350 centistokes | 0–15 |

Formulation 2: Raloxifene capsule

| Ingredient | Quantity (mg/capsule) |
| --- | --- |
| Raloxifene HCl | 10 |
| Starch, NF | 103 |
| Starch flowable powder | 225.3 |
| Silicone fluid 350 centistokes | 1.7 |

Formulation 3: Raloxifene capsule

| Ingredient | Quantity (mg/calpsule) |
| --- | --- |
| Raloxifene HCl | 50 |
| Starch, NF | 150 |
| Starch flowable powder | 397 |
| Silicone fluid 350 centistokes | 3.0 |

The specific formulations above may be changed in compliance with the reasonable variations provided. o A tablet formulation is prepared using the ingredients below:

Formulation 4: Tablet

| Ingredient | Quantity (mg/tablet) |
| --- | --- |
| Danazol | 100–400 |
| Cellulose, microcrystalline | 200–650 |
| Silicon dioxide, fumed | 10–650 |
| Stearate acid | 5–15 |

The components are blended and compressed to form tablets.

Alternatively, tablets each containing 100–400 mg of danazol are made up as follows:

Formulation 5: Tablet

| Ingredient | Quantity (mg/tablet) |
| --- | --- |
| Danazol | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

Danazol, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 100–400 mg of medicament per 5 ml dose are made as follows:

Formulation 6: Suspension

| Ingredient | Quantity (mg/5 ml) |
| --- | --- |
| Danazol | 100–400 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Composition 1: Capsule

| Ingredient | Quantity (mg/capsule) |
| --- | --- |
| Danazol | 250 |
| Formula II compound | 50 |
| Avicel pH 101 | 50 |
| Starch 1500 | 117.50 |
| Silicon Oil | 2 |
| Tween 80 | 0.50 |
| Cab-O-Sil | 0.25 |

Composition 2: Capsule

| Ingredient | Quantity (mg/capsule) |
| --- | --- |
| Danazol | 250 |
| PTH (1–84) or (1–34) | 0.1–1000 |
| Avicel pH 101 | 82.50 |
| Starch 1500 | 90 |
| Silicon Oil | 2 |
| Tween 80 | 0.50 |
| Cab-O-Sil | 0.25 |

Formulation 3: Capsule

| Ingredient | Quantity (mg/capsule) |
| --- | --- |
| Danazol | 250 |
| Formula II compound | 50 |
| PTH (1–84) or (1–34) | 0.1–100 |
| Avicel pH 101 | 50 |
| Starch 1500 | 117.50 |
| Silicon Oil | 2 |
| Tween 80 | 0.50 |
| Cab-O-Sil | 0.25 |

The particular dosage of a compound of formula I, particularly raloxifene, with or without the coadministration of a bone anabolic agent, particularly PTH (1–84) or (1–34), required to minimize the bone loss effect of danazol according to the present invention will depend upon the severity of the condition, the route of administration, and related factors which will be decided by the attending physician.

Generally, accepted and effective daily doses of a formula I compound will be from about 0.1 mg to about 1000 mg/day, and more typically from about 50 mg to about 250 mg/day. Such dosages will be administered to a mammal in need of treatment from once to about three times each day, or more often as needed to effectively treat the present indication. It, usually, is preferred to administer a formula II compound in the form of an acid addition salt, especially, via the oral route.

Preferred dosages, routes of administration, and frequency of administration of danazol and bone anabolic agents are well established and known to those of ordinary skill in the art.

TEST PROCEDURES

Bone Loss I

It is well established in the literature that the ovariectomized rat model is a reasonable model for studying bone loss, particularly osteopenia observed in estrogen-deficient states such as postmenopausal osteoporosis [see, e.g., Wronski, T. J., et al., *Cells Mater, Supp,* 1:69–74 (1991)]. Because the bone loss observed in this model is reflective of the bone loss similar to that induced by the administration of danazol, administration of a formula I compound, with or without a bone anabolic agent, or coadministration of a bone anabolic agent without a compound of formula I, demonstrates the efficacy of the administered compounds for minimizing the bone loss associated with danazol.

Bone Loss II

In the same bone loss model as in Bone Loss I, an alternating schedule of dosing with a danazol, followed dosing with a compound of formula I, would demonstrate the conservation of bone mass relative to a regimen of continuous dosing of danazol. Specifically, ovariectomized rats are treated with danazol at 5 mg/kg per day, P.O., for 21 days. The test group is then dosed with raloxifene at 1–5 mg/kg P.O. for 14 days. After this period, the animals are again treated with danazol followed by raloxifene. This cyclic therapy is continued for a total of six months.

Bone Loss III

Fifty women suffering from diagnosed endometriosis are chosen for this study. These women are generally in good health. Women receiving hormonal therapy (estrogens, progestins, or GnRH) for any reason are excluded from the study.

Since endometriosis is isosyncratic, diagnosis is carefully made on each individual and a variety of parameters are evaluated. Analysis of each of these individual parameters, from the parent's initial entry into the study to their final exit from the study, are carefully noted so that the results of the clinical trial are properly interpreted. The parameters listed are not all essential, but there must be at least several defining factors. The parameters for endometriosis which may be monitored include, for example, pelvic pain, CT, MRI or ultrasound scans of the pelvic area, blood levels of $CA^{125}$, and/or laparoscopy.

Similarly, the negative side-effects, particularly bone loss, are also monitored in each individual throughout the course of the study. Bone loss (osteoporosis) can be monitored by DEXA (Dual Energy X-ray Analysis) as well as measuring urinary excretion of hydroxyproline, pyridinoline cross-links, calcium, and/or creatinine.

The patients are given danazol twice daily at a dose of 200 mg via the oral route. This would continue for a period of one year. During the course of this therapy both the parameters for endometriosis and side-effects would be monitored on a monthly basis. At the first sign of the onset of side-effects (usually defined as 10–20% loss of bone density), the patient would cease receiving danazol and begin receiving raloxifene at a dose of 50–150 mg per day P.O. and/or a bone anabolic agent at the standard dosage, for the remainder of the study.

Bone Loss IV

This clinical application is similar to the procedure described above in Bone Loss III, but this study is a prevention study whereas the above described procedure is a treatment study.

The patients in this study would receive danazol at 200 mg, twice a day P.O., every other month beginning with the first month. In alternate months, these patients would receive 50–250 mg of raloxifene P.O. daily, with or without appropriate administrations of a bone anabolic agent. The time course of the study would be one year.

We claim:

1. A method for minimizing the bone loss effect of a compound of formula II

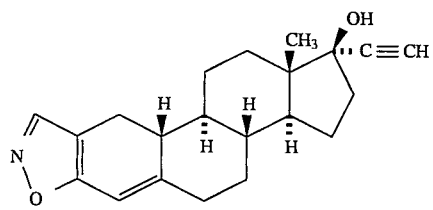

or a pharmaceutically acceptable salt thereof, wherein said formula II compound is administered to a mammal in need of treatment, comprising concurrently administering to said mammal an effective amount of a compound of formula I

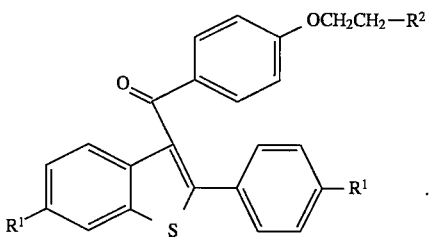

wherein
each $R^1$ is independently —OH, —$CH_3$, —$OCOC_6H_5$, or —$OCO(C_1$–$C_6$ alkyl); and
$R^2$ is 1-piperidinyl, 1-pyrrolidinyl, or 1-hexamethyleneimino; or a pharmaceutically acceptable salt thereof.

2. A method according to claim 1 wherein each $R^1$ is —OH, and $R^2$ is 1-piperidinyl, or a pharmaceutically acceptable salt thereof.

3. A method according to claim 2 wherein said mammal in need of treatment of a compound of formula I is a human female.

4. A method according to claim 3 wherein said female is suffering from endometriosis.

5. A method for minimizing bone loss comprising the method of claim 1 and further comprising administering to said mammal an effective amount of a bone anabolic agent.

6. A method according to claim 5 wherein each $R^1$ is —OH, $R^2$ is 1-piperidinyl, or a pharmaceutically acceptable salt thereof, and said bone anabolic agent is parathyroid hormone (1–84) or (1–34).

7. A method according to claim 6 wherein said mammal in need of treatment of a compound of formula I is a human female.

8. A method according to claim 7 wherein said female is suffering from endometriosis.

9. A pharmaceutical composition comprising a compound of formula II

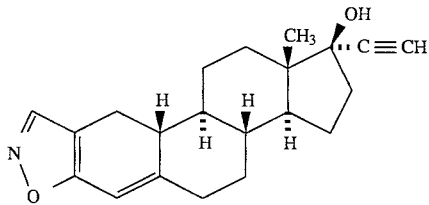

or a pharmaceutically acceptable salt thereof, a compound of formula I

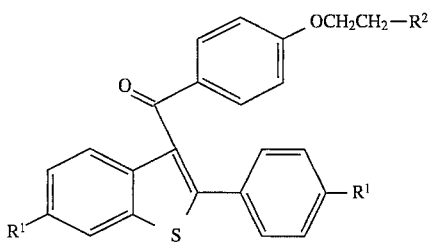

wherein each $R^1$ is independently —OH, —$CH_3$, —$OCOC_6H_5$, or —OCO ($C_1$-$C_6$ alkyl; and $R^2$ is 1-piperidinyl, 1-pyrrolidinyl, or 1-hexamethyleneimino; or a pharmaceutically acceptable salt thereof; and optionally, a bone anabolic agent, in combination with a pharmaceutically acceptable carrier, diluent, or excipient.

10. A pharmaceutical composition according to claim 9 wherein each $R^1$ is —OH, and $R^2$ is 1-piperidinyl, or a pharmaceutically acceptable salt thereof.

11. A pharmaceutical composition according to claim 10 wherein said optional bone anabolic agent is parathyroid hormone (1–84) or (1–34).

12. A pharmaceutical composition according to claim 10 wherein said composition is used for minimizing bone loss from administration of said formula II compound.

* * * * *